United States Patent [19]

Pitman et al.

[11] Patent Number: 4,530,246
[45] Date of Patent: Jul. 23, 1985

[54] METHOD AND APPARATUS FOR IDENTIFYING FRACTURED BRITTLE ARTICLES

[75] Inventors: Kelvin G. Pitman, Newbury; David A. Grime, Preston; Malcolm R. M. Knight, Newbury, all of England

[73] Assignee: Metal Box Public Limited Company, Reading, England

[21] Appl. No.: 466,352

[22] PCT Filed: Jun. 10, 1982

[86] PCT No.: PCT/GB82/00173
§ 371 Date: Feb. 7, 1983
§ 102(e) Date: Feb. 7, 1983

[87] PCT Pub. No.: WO82/04482
PCT Pub. Date: Dec. 23, 1982

[30] Foreign Application Priority Data
Jun. 16, 1981 [GB] United Kingdom ............ 8118530

[51] Int. Cl.³ ............................................. G01N 22/02
[52] U.S. Cl. ..................................... 73/799; 73/644; 73/801
[58] Field of Search .............. 73/587, 799, 801, 644

[56] References Cited

U.S. PATENT DOCUMENTS 3,924,456 12/1975 Vahaviolos ........................... 73/770
4,077,254 3/1978 Mercer, Jr. et al. .
4,089,224 5/1978 Scott et al. ........................... 73/587
4,090,400 5/1978 Vahaviolos ...................... 73/582 X

FOREIGN PATENT DOCUMENTS

2633680 2/1978 Fed. Rep. of Germany .

Primary Examiner—Jerry W. Myracle
Attorney, Agent, or Firm—Cushman, Darby & Cushman

[57] ABSTRACT

Apparatus for automatically inspecting brittle articles such as containers of glass and the like has element (50) which applies a force to each article in turn, so as to propagate any cracks in the glass. Ultrasonic vibrations created during the propagation of a crack is transmitted via a constant laminar stream of liquid (76) from which the vibrations are received by a transducer head (94) of the crack detection equipment, which triggers an alarm, a visual display and/or an automatic marking or rejection device.

16 Claims, 28 Drawing Figures

METHOD AND APPARATUS FOR IDENTIFYING FRACTURED BRITTLE ARTICLES

FIELD OF THE INVENTION

This invention relates to methods and apparatus for identifying as fractured an article of brittle material, or articles of brittle material in a succession of generally-similar articles, the invention being concerned primarily with the automatic inspection of brittle articles in industrial manufacturing processes. Such a process may comprise the manufacture of the brittle articles themselves, or for example other processes such as the filling of the articles where the articles are in the form of containers.

The term "fractured" and any reference to a fracture herein, where the context permits, are to be understood to refer to any structural fault, within the brittle material itself, such that, if a suitable force is applied to the material so as to set up in the material a stress (which may be compressive, tensile or torsional, and which may be linear or in the form of a hoop stress), the effect of such stress will be to enlarge the structural fault rather than a mere change of dimensions by way of strain. Such faults may take the form of a crack, a chip, a bubble or other flaw in manufacture, such as to produce a weak zone or stress raiser in a manner not contemplated during design of the article.

The term "brittle" is to be interpreted in this light also, i.e. a "brittle" material as referred to herein means a material in which such a fault, if pre-existing, will tend to propagate upon internal stress being induced. Examples of such materials include glass, ceramics and many plastics materials.

Articles to which the invention is applicable include (by way of non-limiting example): glass containers such as bottles, jars, flame-sealed ampoules or laboratory glassware; fine glass articles such as decorative lead-crystal glassware; ceramic articles such as pottery, earthenware, porcelain or china; ceramic components such as insulators for spark plugs or other purposes, bearings and refractory components for industrial or similar uses; moulded plastics components such as cases for electronic equipment; plastics bottles and other containers made of plastics.

BACKGROUND OF THE INVENTION

The inspection of brittle articles may be carried out in a number of different ways, of which simple visual inspection is perhaps the most common. Apart from visual inspection, there are on existence, or there have been proposed, automatic or semi-automatic techniques for inspecting glass bottles and jars so as to detect flaws such as cracks. Such techniques are generally optical in nature and rely on light-scattering phenomena.

In connection with fine, hand-made circular glass and ceramic ware, particularly articles such as vases, bowls, drinking glasses, cups, plates and the like, it is common practice to test the finished article (after firing in the case of ceramics) for soundness by applying a light, sharp impact with the fingers, so as to cause the article to resonate with an audible note. The skilled operative can tell from the quality of this note whether there is any fault in the article. The principle of using resonant vibration in the audio range, produced by impact, is applied to a proposal for repetitive industrial inspection of one specific product, viz. plastics-coated glass bottles, contained in the United Kingdom patent (GB-A-1416082) granted to Dart Industries Inc. In the method described in GB-A-1416082, a positive impact force is applied to the bottle, and the intensity of the vibrations within the audio range 50 Hz-10,000 Hz, emitted by the bottle after a predetermined lapse of time, is then detected, by means of a transducer in contact with the bottle, and measured. In a good bottle, i.e. one having no cracks, the intensity after the pre-determined time lapse is known for any particular design and size of bottle and a given impact force, so that this value of the intensity may be used as a datum. If the bottle is cracked, the resonance will be damped by the crack; therefore if the intensity after the predetermined time lapse is significantly less than the datum value, the bottle is identified as being cracked.

It should be noted that the method of GB-A-1416082 must depend for its reliability on the comparison, between the sonic intensity produced in a given bottle and that used as a datum value, being itself a reliable criterion. This in turn requires that each bottle tested must, in its undamaged state, display no more than a small variation from the characteristics adopted for the "datum" bottle. In this connection, there is commonly found, in the manufacture of glass articles by mass production methods, a substantial variation in various dimensions, such that the intensity of the audible resonance, at the point on the article chosen for contact with the transducer, may show some considerable variation even in the absence of a crack. Close control of dimensional variations therefore may need to be applied.

In addition, the need to apply an impact force to a brittle article, whilst not dangerous in the case of a fine handmade article whose degree of symmetry is likely to be high (so that the force can be very small indeed and still produce an easily-detectable note), may often be dangerous in the case of articles made by repetitive industrial processes. This is because the magnitude of the impact force must be sufficient to produce resonance on all of a succession of articles, regardless of any dimensional variations, and will therefore need to be more substantial than in the case quoted above.

In addition, a method such as that proposed in GB-A-1416082 is only suitable in respect of articles whose shape is such that they will resonate in the audio range of frequencies when struck. This in general restricts the application of such a method to articles which are generally circular. Even then, it is not in general applicable to any article which is in a condition such that any resonance will be damped to a degree at which it cannot be effectively measured. This applies for example to many containers which have been filled with a product (particularly a solid or heavy viscous liquid product).

Once a container has been filled, it is desirable for a number of reasons to apply a closure immediately; and a filled container, for present purposes, implies a container that has an appropriate closure secured on to it; whilst a closed container implies a filled container.

Closed containers of glass or other brittle material are not in practice usually subjected to inspection for damage, other than visual inspection. In fact, since glass, if handled with reasonable care, is quite strong, a closed glass bottle or jar is unlikely to suffer damage, other than outright breakage, between the completion of the closing process and initial removal of the closure by the eventual consumer. This is probably because the most vulnerable part of the container is its neck or "finish" to which the closure is secured, since the closure extends around and over the finish and affords it some considerable measure of mechanical protection.

In this connection it should be noted that in this specification reference to closures means more particularly closures, of plastics or metal, of the kind generally referred to as caps, i.e. those which do have an external skirt. This is not, however, to be taken to exclude the applicability of the invention to use, if desired, in connection with bottles having corks or other similar closures that serve purely as a plug and which do not have an external skirt.

Nevertheless, problems have arisen in connection with certain kinds of cap in that fracture is found to be present occasionally in the neck or finish of the glass container after a cap has been applied. This fracture takes the form of cracking, often giving rise to only a very small crack but sometimes sufficient to cause a piece of glass actually to separate from the remainder of the container. This piece of glass will usually be held in place by the cap but will fall off, either externally or into the container itself, when the container is eventually opened. Fractures are found to occur during the actual capping process, and a problem arises in that, because they are generally in a part of the container hidden by the cap, inspection by known methods relying on the use of light, such as are mentioned above, is either difficult or impossible.

The use of acoustic waves emitted by various materials—commonly referred to as acoustic emission as an aid to detecting cracks in certain materials is known per se. It has for example been proposed for such purposes in connection with the bonding of electronic components, or in inspecting welds in metal; riveted, brazed or soldered joints in metal; and indeed in connection with any metal-working application in which areas of high stress, liable to give rise to cracking of the metal, are set up.

The stress waves which constitute the so-called "acoustic" emission travel outwardly from their source in the form of spherical waves and are generated whenever the material concerned is under stress, and not only when it cracks or otherwise fractures. However, in the event of fracture, energy is of course dissipated at a higher rate than if the stresses occurring are such as not to cause fracture. There are commercially-available acoustic emission crack detector systems which are used for the detection of fractures in the materials mentioned above. These systems can measure the magnitude of acoustic emission in terms of various parameters; as is the case in the systems disclosed in GB-A-1416082 and discussed above, the parameters for any particular practical application are chosen, according to the requirements of the user, to suit best the particular material and stress levels concerned, and according to the kind of information required.

Many of the materials referred to above are not "brittle" in the sense in which the term is used herein; the systems referred to are concerned with individual inspection of components rather than with the automatic monitoring of products being produced repetitively at high speed in a production line.

DISCUSSION OF THE INVENTION

It will be evident from the foregoing that there is a need for a versatile method of monitoring automatically an industrial output of brittle articles (as hereinbefore defined), particularly when the articles are being produced or processed in rapid succession and are generally similar to each other.

It is desirable that such a method should not be required to rely on a comparison between the magnitude of a detected signal on the one hand, and, on the other hand, a datum value which may be unreliable due to variations in dimensions or other characteristics, as between one article and another. Accordingly a method is desirable in which a positive signal, which may be characteristic of only a single article is yet indentifiable as an indication of an unwanted fault.

Furthermore, such method should not rely on optical methods, since the fault may be hidden. Nor should it rely on the ability of the article to resonate in response to impact or other applied stress; thus enabling the method to be applied to articles of a shape such that resonance is substantially absent, and to those (such as some filled containers) in which any resonance is damped out.

In addition, the method should desirably be such that ability to detect faults is not affected by the rate of loading, i.e. by whether or not an impact is applied to the article.

According to the invention, in a first aspect, a method of identifying as fractured an article of brittle material includes the steps of applying a force to the article to induce a stress therein of a magnitude such as to propagate, by enlargement, a pre-existing fracture in the article, and, whilst the force is being applied, detecting ultrasonic vibrations produced directly and only by the propagation of the fracture itself. The ultrasonic vibrations detected are preferably of a frequency of 2 MHz or less, but are greater than 10,000 Hz in frequency.

A principal difference between this method, and that disclosed for example in the Dart Industries patent GB-A-1416082 discussed in the preceding section, is that, whereas the latter utilises vibrations produced by resonance in the audio range, the method of the present invention is not only not concerned with audio frequencies at all, but causes any fault in the brittle article to become enlarged. This enlargement sets up vibration in the material of the article, due to the sudden release of strain energy as the crack (or other flaw) increases in size. In the case of a crack, this energy is released at the tip of the enlarging crack. This energy, in the form of the vibrations which include, either at tonic or harmonic frequencies, those which are detected so as to identify the article as being fractured, is transmitted through the material of the article; but it should be noted that this transmission is in general not a manifestation of resonance.

In a second aspect, the invention provides apparatus for identifying as fractured an article of brittle material, the apparatus comprising: article-supporting means for supporting a said brittle article; force-applying means adjacent the article-supporting means; means for effecting relative movement between the article-supporting means and the force-applying means whereby to cause a force to be applied by the latter to a said article supported by the former such as to induce a stress in the article of a magnitude such as to propagate by enlargement, a pre-existing fracture in the article; and ultrasonic vibration-detecting means positioned adjacent to the force-applying means for detecting, whilst the force is being applied, to ultrasonic vibrations produced directly and only by the propagation of the fracture itself. The vibration-detecting means preferably comprise: transducer means for transmitting electrical signals in response to said ultrasonic vibrations; mounting means mounting the transducer means and providing means for physically connecting the transducer means with a brittle article supported by the article-supporting means and engaged by the force-applying means whereby said ultrasonic vibrations are transmissible instantly to the transducer means; and functional means connected electrically with the transducer means for performing at least one predetermined function in response to said electrical signals. Typically, the transducer means comprises a piezo-electric transducer.

The ultrasonic vibration takes the form of a spherical wave propagating from the site of fracture. This wave will propagate through solids and also through fluids which are not in turbulent flow. The requirement that the vibrations induced in a faulty article shall be detectable, e.g. by a piezoelectric transducer, presupposes that the latter is not separated from the former by the atmosphere of the workshop, which may be in turbulent flow. However, although the transducer may be arranged so that, in the position at which detection of fractures takes place, it is in direct contact with the article itself, this is not essential; the acoustic emission wave may be transmitted through, for example, parts of the apparatus itself, and the transducer mounted accordingly in the most convenient position thereby made possible.

According to a preferred feature of the invention, the step of detecting the ultrasonic vibrations comprises directing a stream of liquid, in a state of substantially laminar flow, against the brittle article whereby vibrations from the article are transmitted backwardly along the liquid stream, and detecting the said vibrations in the liquid stream by means of a transducer. Accordingly, the apparatus in its preferred forms comprises: flow means for directing a stream of liquid, in a state of substantially laminar flow, against a brittle article supported by the article-supporting means and engaged by the force-applying means; transducer means associated with the flow means for transmitting electrical signals in response to said ultrasonic vibrations transmitted backwardly along said liquid stream from the brittle article; and functional means connected electrically with the transducer means for performing at least one predetermined function in response to said electrical signals. The use of a stream of liquid (preferably water), as the means for transmitting the ultrasonic vibrations away from the brittle article, is particularly advantageous. It avoids the need to ensure that the piezo-electric transducer is in intimate contact with the article; this is a valuable advantage where a large number of articles are to be inspected automatically in rapid succession. Use of a stream of liquid in laminar flow also ensures that the transducer itself can be mounted so as to receive vibrations direct from the liquid, so that not only the interface between the article being inspected and the liquid stream, but also that between the latter and the transducer, can readily be made free of any air gap. This method minimises extraneous "noise", and consequently improves the sensitivity which it is possible to obtain with the apparatus.

Preferably the laminar stream of liquid is maintained in continuous flow, the brittle article (or each in turn) being introduced into said stream and the force being applied to the article whilst the article is in the stream.

The "functional means", mentioned above, may take any suitable form. In general it comprises electronic equipment, for amplifying the signal from the transducer whilst filtering out extraneous "noise", and which may for example be coupled with an audible or visual alarm device for indicating a faulty article. Preferably the functional means includes an automatic rejecting mechanism for faulty articles; to this end, the apparatus preferably includes means defining an acceptance path for articles failing to produce said ultrasonic vibrations when a force is applied to it by the force-applying means, and means defining a rejection path for an article producing said vibrations, the said functional means comprising means for directing said article selectively into the acceptance path or the rejection path according to the absence or presence of said ultrasonic vibrations.

It is important to note that the applied force may take any suitable form. Whilst typically it may be compressive, in some applications an applied tensile, shear or bending force may be found more appropriate, whilst in other applications still it may be advantageous to apply a torque to the article. Thus, for example, where the article is cylindrical or of another shape defining a central axis of the article, the method is characterised in that the step of applying a force to the article comprises applying a torque thereto abouts its central axis.

It should be understood that the method may include the application of any combination of two or more of the types of loading possible, viz. compressive, tensile, shear or bending forces or torque. Preferably, however, at least a compressive load is applied; furthermore, such compressive load is preferably applied to the article in a direction such as to induce stresses having components directed within the article in at least two dimensions. In the case where the article has a central axis, as mentioned above, a compressive load is preferably applied axially of the article.

However, it should be noted that alternatively, or in addition, a load or loads may be applied radially, laterally or in any other required direction. In this connection it should be noted, taking a glass bottle as a typical example of a brittle article to be inspected, that a loading applied axially will give rise to stresses within the bottle which are predominantly compressive, but which will for example include hoop stresses. Stressing of the bottle due to axial loading, if the bottle is supported upright, will arise throughout the material of the bottle.

It is sometimes necessary, however, to ensure that flaws in the article can be detected wherever they happen to be; and in many cases a simple force applied axially will not be sufficient to stress the fault in the correct direction to enable it to propagate. This is partly because in the region of the fault there may be residual stresses in the material which may actually be wholly or partly cancelled out by stresses resulting from the application of a force. Furthermore (taking once again the example of a glass bottle), if the bottle is supported upright, a force applied radially may not give rise to stresses throughout the material of the bottle, and will in any case not give rise to stresses displaying any degree of uniformity unless the applied force is distributed over the whole height of the bottle.

This, as will be seen shortly, lends emphasis to an important distinction between the method and apparatus of the present invention and those of prior art arrangements which utilize the resonance of the article, viz. that since resonance of the article need not be taken into account, it is possible, where desired, to provide the force-applying means over such an area of the surface of the article that any tendency for its natural resonance to assert itself is effectively damped; and furthermore, the article may be of such a shape or character that is has little or no characteristic natural resonance.

Accordingly, the force-applying means may include an article-engaging surface or surfaces such as to engage over substantially the whole of the exterior surface (or interior surface, if any) of the article. In one embodiment, to be described later herein by way of example, there is provided an axial force-applying member which co-operates with means for applying radial forces over the whole height of an article whose external shape is that of a surface of revolution about a central axis. The means for applying radial forces comprises, in such an embodiment a resilient member which is forced into force-applying conformity with the contours of the article by application of fluid pressure behind the resilient member.

In general the force-applying means has at least one force-applying surface for engaging a said article, said surface or surfaces being so orientated as to apply the said force to the article in a direction or directions such that the stresses induced thereby in the article have components directed in at least two dimensions. Such components of stress may be a complex combination of tensile or compressive linear, or hoop stresses. In preferred embodiments, there is provided a single force-applying member for applying an axial force to the article, this single member being so shaped that it applies force in the direction giving rise to multi-directional stress components within the article.

To this end, this member preferably has at least one said force-applying surface inclined with respect to a direction of relative linear movement between the force-applying member and the article-supporting means. In the typical and preferred case when the apparatus is for the high-speed automatic inspection of a succession of generally-similar brittle articles, carried by the article-supporting means along a path defining an inspection station at which the liquid stream (or other means for receiving the ultrasonic vibrations from the article), and the force-applying means, are situated, the force-applying means comprises a rolling member rotatable about its own axis and biassing means operatively connected with the rolling member, the axis of the latter being transverse with respect to the said path and the biassing means being arranged to apply a resilient biassing force to the rolling member having a major component perpendicular to said axis and to said path.

Such rolling member preferably has, for engaging each said article in turn, at least one coaxial force-applying surface having a generator inclined with respect to said major component of the biassing force, whereby to apply said force to the article in a direction such that the stresses induced in the latter have components both parallel and transverse to the said major component. It is advantageous in such a case to provide, particularly where the article defines a central axis, that the article is rotated at least once about its central axis, at least whilst the force is being applied to the article, whereby a radial component of said force is directed over the entire periphery of the article. This ensures that the asymmetrical stresses resulting from the application of the forces by the rolling member are applied around the whole of the article. Such rotation may be readily effected by any suitable means for applying an appropriate torque to the article.

In this connection it should be noted that where a torque is applied to the article, this may be such as to induce rotation of the latter without giving rise to any significant torsion or the apparatus may be arranged so as to restrain the article at least or partially against rotation so that a torque is induced within the article.

It should be noted that the magnitude of the load applied by the load-applying means will be chosen as the optimum for each application. The extent to which such load consists of an impact, i.e. a dynamic load rather than a static load, is found to be immaterial since the rate of application of the applied force is not relevant to the effectiveness of the method provided its magnitude, position and direction are such that the resulting stresses, induced in the article, cause propagation of any faults and so give rise to the required ultrasonic vibrations.

It will be understood that the natural frequency of the piezoelectric transducer, that transmits the output signal representing the acoustic emission to the functional means such as indicating equipment, is preferably chosen so as to be in or close to the range of ultrasonic frequencies characterizing the induced vibrations in the material being tested, so that the incidence of fracture conditions is represented as emphatically as possible in the output signal.

The invention is suitable for detecting faults that may arise during the process of applying a closure to a brittle container. Accordingly, the apparatus must be incorporated in a capping machine or arranged adjacent to it, in a position along the path followed by the containers in which the capping operation takes place. Capping machines may be of an in-line type to which containers are supplied by an indexing conveyor or other suitable transfer device, the capping operation taking place on each successive container whilst the latter is stationary. The liquid stream and it associated transducer, for receiving vibrations from the containers are arranged close to the container. The load-applying means in this case is or includes the capping head itself. The same remarks apply to another type of capping machine, namely a high-speed machine in which the bottles are fed to a turret rotating on a vertical axis. The turret is either indexed between a number of stations including a capping station (preceded by one or more filling stations and a station at which the cap is fed to the machine and placed lightly on the container); or rotated at constant speed. In the former case the capping head may be stationary at the capping station, whereas in the latter case it is mounted on the turret and rotates therewith. In either case, the liquid stream will preferably be directed at the container at each station, and to this end it preferably takes the form of a number of jets emitted from stationary nozzles, one at each station of the machine.

Apparatus according to the invention is suitable for the in-line monitoring of glass bottles at production rates up to at least six hundred per minute.

DESCRIPTION OF THE DRAWINGS

The invention will now be further explained, and embodiments thereof described, by way of example only, with reference to the accompanying drawings, in which:

FIG. 3 is a diagram in two parts, whereof FIG. 3(a) illustrates the effect on cracks in a hollow brittle article of radial forces applied when the cracks are in a first orientation, whilst FIG. 3(b) illustrates the effect when the cracks are in a second orientation;

SPECIFIC DESCRIPTION

Figure 1:
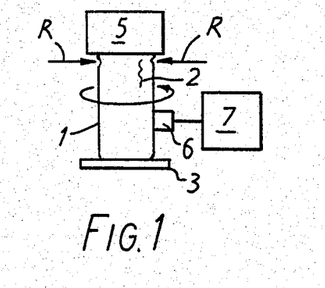
FIG. 1 is a diagram illustrating the basic principle of the invention when applied to a brittle article in the form of an empty glass jar, supported on a conveyor seen in end elevation.
Figure 2:
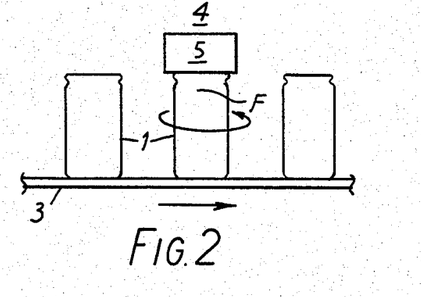
FIG. 2 is a similar diagram to FIG. 1 but seen in side elevation.

Referring first to FIGS. 1 and 2, an article in the form of an empty cylndrical jar 1, made of glass, has a crack indicated at 2. The jar is supported by a moving conveyor 3 which carries it through an inspection station 4. The jar is one of a succession of generally-similar jars. At the inspection station 4, an axial force F is applied, by force-applying means diagrammatically indicated at 5, to the top of the jar, whilst radial forces R are applied, by means not shown, to the neck of the jar. The forces F and R cause the crack 2 to propagate by becoming enlarged from its tip. This propagation gives rise to spherical stress waves which manifest themselves in the form of ultrasonic vibrations. These vibrations are transmitted through the glass to vibration-detecting equipment comprising means 6 for receiving the vibrations from the jar, with which the means 6 is in close contact, and for transmitting appropriate electrical signals to a functional unit 7, which may take a number of forms such as those described later herein with reference to FIG. 9.

Figure 3:
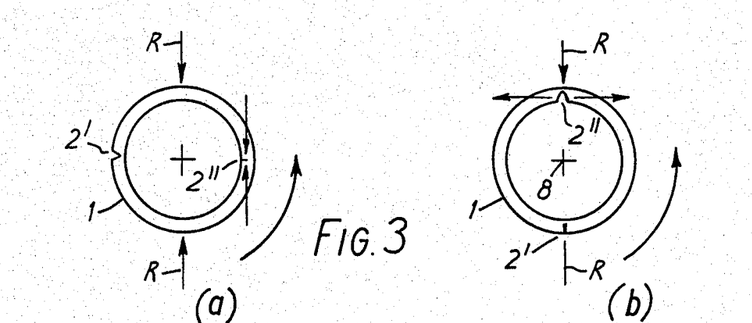

Referring to FIG. 3, in FIG. 3(a) there are shown two cracks, viz. a crack 2' in the outer surface of the jar 1, and a crack 2" in the inner surface diametrically opposite the crack 2'. The radial forces R' are applied compressively to the jar in the transverse plane perpendicular to that containing the two cracks. The hoop stresses set up in the jar by the forces R are such that the crack 2' on the outer surface will tend to be opened up (and will therefore tend to become enlarged). However, the crack 2", on the inner surface, will tend to be closed up so that the induced hoop stresses do not have the desired effect. If reference is now made to FIG. 3(a), it will be seen that if the jar 1 is rotated through 90° about its central axis 8, the opposite effect applies, viz. that the crack 2" on the inside surface is opened up whilst that on the outer surface tends to close.

Therefore, referring again to FIGS. 1 and 2, where the forces R' are applied radially in a single plane, the jars 1 are rotated each about its own axis (by means not shown) at the inspection station 4 in order to ensure that any flow in the jar neck that may be caused to propagate under the influence of the radial forces R is allowed to do so.

Figure 19:
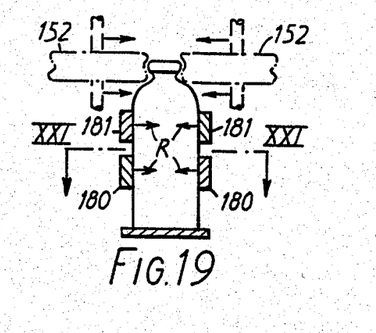
FIG. 19 is a diagram illustrating means whereby a torque may be applied to an article being inspected by a method according to the invention.

The radial forces R may be applied by means of rollers similar to those shown in phantom lines in FIG. 19, these rollers being biassed towards the jar 1 by suitable means such as springs. Alternatively, a similar effect may be obtained by use of a single force-applying member 10, FIG. 4.

Figure 4:
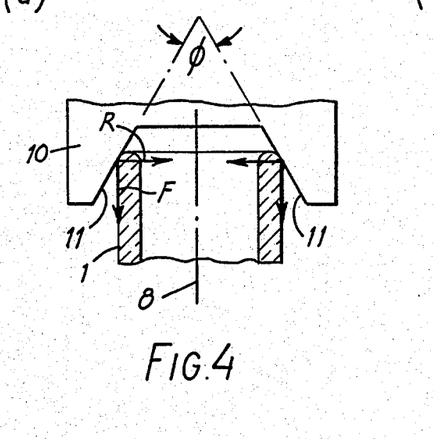
FIG. 4 is a digrammatic cross section illustrating the application of axial and radial crack-propagating components of force to a brittle article by means of a single force-applying member in apparatus according to the invention.

Referring to FIG. 4, the member 10 is arranged for relative axial movement with respect to the jar 1. It has jar-engaging surface portions 11 which are inclined with respect to the jar axis 8. Preferably the surface portions 11 subtend an angle 0 of 60 degrees, though the value of this angle may be chosen as desired. The force applied to the jar 1 by the member 10 has a radial component R and a horizontal component F; each of these components sets up stresses in the jar 1. The surface portions 11 may take a number of different forms, two of which will be described later herein with reference, respectively, to FIGS. 5 to 7 and FIG. 16.

Figure 5:
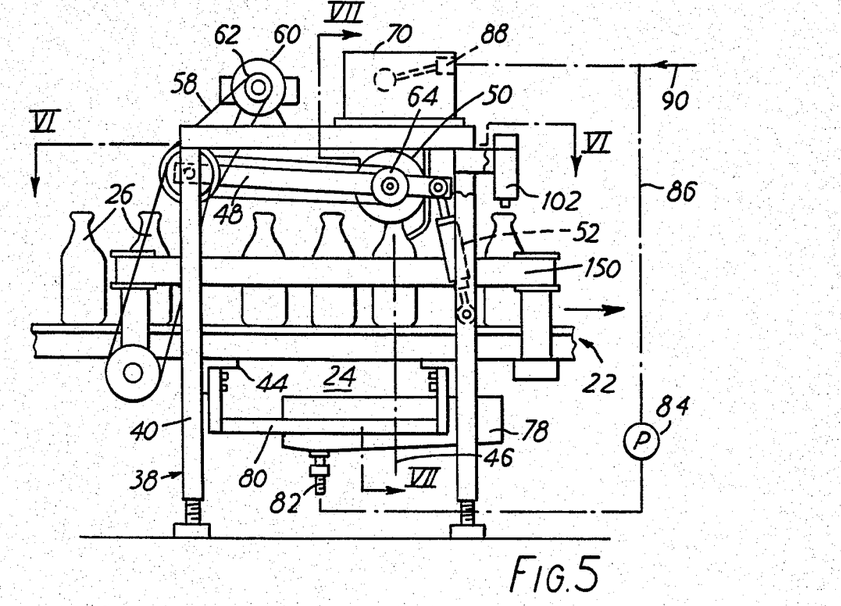
FIG. 5 is a simplified side elevation of one apparatus according to the invention, in the form of an on-line automatic inspection unit for glass bottles.
Figures 6, 7, 8:
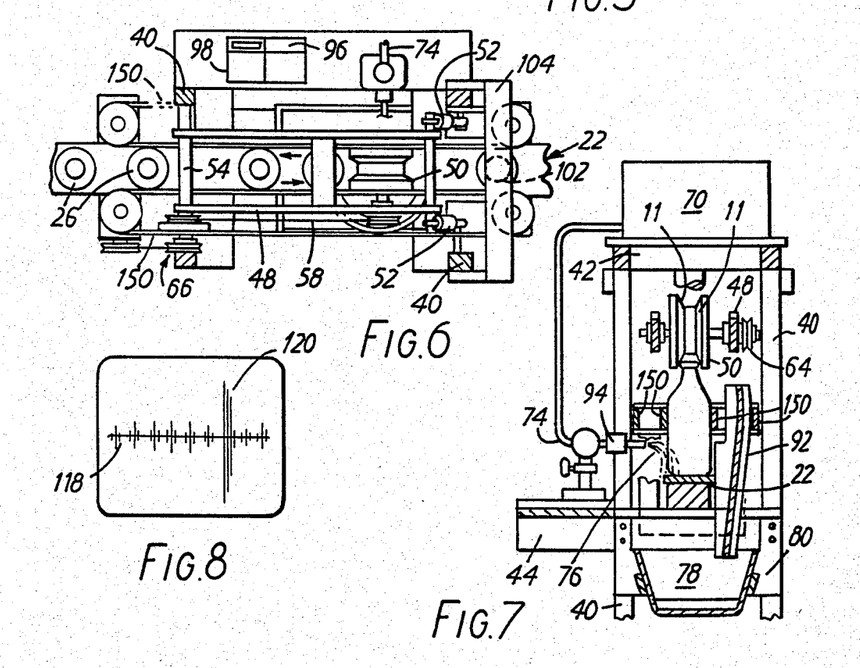
FIG. 6 is a simplified plan view, taken in section on the line VI—VI in FIG. 5.
FIG. 7 is a simplified sectional end elevation taken on the line VII—VII in FIG. 5.
FIG. 8 shows a typical moving trace on a visual display unit obtainable using the apparatus shown in FIGS. 5 to 7 and FIG. 9.

Referring now to FIGS. 5 to 7, there is shown therein an automatic, high-speed inspection unit 24 for detecting cracked bottles from among a succession of empty glass milk bottles 26 passing at a rate of up to 600 per minute along a continuously-moving conveyor 22.

The conveyor 22 is straddled by a gantry 38 comprising two side portal frames 40 with top cross-members 42 and a pair of stretchers 44 which are secured to the frame of the conveyor 22. The stretchers 44 are adjustable for height, so that the conveyor can be raised or lowered for different sizes of bottle. The conveyor 22 moves at a constant speed through the gantry 38 from left to right as seen in FIGS. 6 and 7, carrying the bottles 26 along a straight predetermined path through the unit 24.

Automatic inspection takes place at a position, along the path of the bottles, defined by a centre plane indicated by the phantom line 46 in FIG. 5.

The unit 24 has force-applying means comprising essentially an arm 48, carrying a load wheel or roller 50 and maintained normally in a state of equilibrium by a pair of resiliently-extensible jacks 52. The arm 48 comprises a frame which may be of synthetic plastics or other material such as to propagate as little vibration as possible, though it may be of metal. At its upstream and higher end the arm 48 is freely pivoted, by means of a cross-shaft 54, to the gantry 38 on an axis transverse to the conveyor 22. The load wheel 50 may be for example of plastics material or of metal. The wheel 50 is rotatable, preferably in nylon bearings, in the arm 48 on its own axis which lies in the plane 46, by means of a band or belt drive 58. The latter is driven continuously by an electric motor 60 which is mounted on top of the gantry 38. The drive 58 is from a motor pulley 62 to a pulley 64 fast on the shaft of the load wheel 50, via a compound pulley 66 freely rotatable on the cross-shaft 54.

The jacks 52 (which for clarity are omitted from FIG. 7) may be of any suitable kind, incorporating springs or being of the pneumatic or hydraulic kind. They are adjustable as to the load which they exert. The lower end of each jack is pivoted to the gantry 38, and their upper ends are pivoted to the upstream or upper end of the arm 48.

The roller 50 is one example of the force-applying member previously designated 10 with reference to FIG. 4. In FIGS. 5 to 7 it has two coaxial force-applying surfaces 11, each having a generator inclined with respect to the major (vertical downward) component of the force exerted by virtue of the jacks 52 on the bottle 26 by the roller 50. In this example the surfaces 11 are frusto-conical, though it will be realised that they may for example be each in the form of a frustum of a sphere.

Also driven by the belt drive 58, via a third element of the compound pulley 66, are a pair of parallel drive belts 150. The belts 150 engage opposite sides of the bottles 26 and are driven in opposite directions as indicated in FIG. 5. In this way they cause the bottles to rotate about their own axis for the reason explained above with reference to FIG. 3.

A water header tank 70, carried on top of the gantry 38, has an outlet pipe 74, of such a bore that the flow rate of water through it is substantially laminar. The pipe 74 terminates in a nozzle for directing a laminar stream 76 of water towards any bottle 26 that is in the position 46 on the conveyor, and is supported by the machine frame by any suitable means, preferably adjustable, both as to its position with respect to the plane 46 and as to the inclination, if any, of the pipe 74 with respect to the horizontal, so that the water stream 76 may be directed in the most beneficial way towards the bottle 26 for the purpose shortly to be described.

A collecting trough 78 is carried by the gantry 38 below the level of the conveyor 22, to collect the water which has issued from the nozzle in the stream 76; the trough 78 is preferably adjustable for height, and, in the example shown, it is carried by brackets 80 attached between the stretchers 44. The collecting trough 78 may optionally have a flexible drain pipe 82 connected, via a water pump 84 and riser 86, to an inlet of the header tank 70. The latter preferably has means 88 for maintaining a constant head of water in the tank and therefore above the outlet pipe 74, the inlet being connected to a water main (by a pipe indicated at 90) for the purpose of receiving make-up water. The pump 84, if provided, may conveniently be driven, directly or via a suitable drive, by the electric motor 60. A curtain or a shield 92 (indicated somewhat diagrammatically in FIGS. 6 and 7 but omitted for clarity from FIG. 5) is preferably provided to deflect into the trough 78 any water from the stream 76 that is not intercepted by a bottle.

Attached to the water pipe 74 is an ultrasonic vibration sensor head 94 (indicated diagrammatically). This comprises a piezoelectric transducer connected with a pre-amplifier 151 (FIG. 9), which is optionally encapsulated with the transducer. The sensor head 94 is mounted adjacent the jet nozzle, as shown, or at any convenient point along the pipe 74, in such a manner that any disturbance in the water flowing along the jet pipe, if in the form of vibrations within the ultrasonic frequency range which the transducer is designed to detect, will be transmitted to the latter. This frequency range has a lower limit of 10 kHz and an upper limit of 2 MHz. The jet pipe 74 is preferably of metal, the transducer being in intimate contact with the exterior surface of the pipe; the latter serves to transmit the ultrasonic vibrations from the water to the transducer.

The frame 38 also carries an electronic crack detector unit 96 which also includes a visual display unit 98. The crack detector unit 96 may be of any suitable known kind for indicating the magnitude of ultrasonic waves.

There may optionally be provided a marker 102 for making a suitable mark on any article (such as a bottle 26) that is found by the inspecting unit to have a fracture. In the embodiment shown, the marker unit is mounted over the conveyor 22 by a beam 104 secured to the gantry 38 at the downstream or exit end of the latter.

Figure 9:
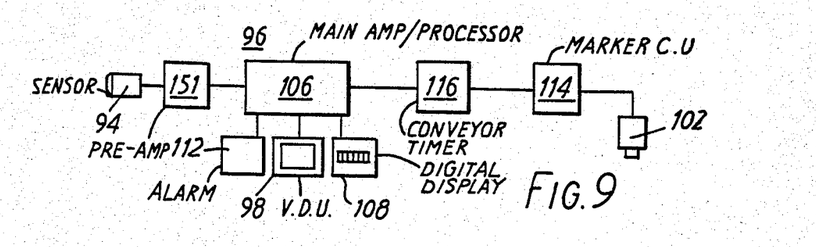
FIG. 9 is a block diagram illustrating various electrical devices for receiving and processing acoustic emission signals obtained in the apparatus of FIGS. 5 to 7.

Turning now to FIG. 9, this shows in block form one possible electrical circuit arrangement for the detection and processing of the ultrasonic emission by the unit 24. The sensor head 94 is connected via the preamplifier 151 to a main amplifier and processor 106 of the unit 96. The function of the processor 106 is to produce a suitable output, representing the magnitude of the ultrasonic emission as detected by the transducer, in terms of required parameters. In the present example the processor is such that its output represents the rate of energy release in the ultrasonic vibrations, this output being supplied to a digital display 108 which indicates numerically the rate at which the energy release exceeds a predetermined threshold value. The threshold value is pre-set by a control, not shown, on the crack detector unit 96, to a value which is sufficiently high to exclude unwanted "noise" but which is well below the minimum value characterising the propagation of a fracture in glass.

The output from the main amplifier and processor 106 is also connected to the visual display unit 108, which gives an oscilloscope trace showing the rate of energy release above the pre-set threshold level, and to a suitable audible and/or visible alarm device 112 arranged to be activated when the processor output exceeds a predetermined value indicating the presence of a fractured bottle.

The marker 102 is actuated by an electronic control unit 114 in response to a signal from the main amplifier/processor 106 indicating a faulty bottle. The marker control unit 114 has inputs connected to a conveyor time 116, which is arranged in any known manner in response to the lapse of time and the speed of travel of the conveyor such that, when triggered by a faulty-bottle signal from the unit 106, the timer delivers a pulse to the marker control unit, so as to operate the marker, when the conveyor has travelled through the required distance to bring the faulty bottle to a position underneath the marker 102.

FIG. 8 shows a typical trace on the screen of the visual display unit 98, moving from left to right as the conveyor moves through the monitoring unit 24. The trace represents, at its extreme left hand end at 118, the ultrasonic vibration level (energy release rate) in respect of the bottle undergoing inspection at the position 46, FIG. 5. The preceding eight bottles are indicated also on the trace, and one of them has had a fracture detected, as indicated by the trace of severely increased amplitude at 120.

Figure 10:
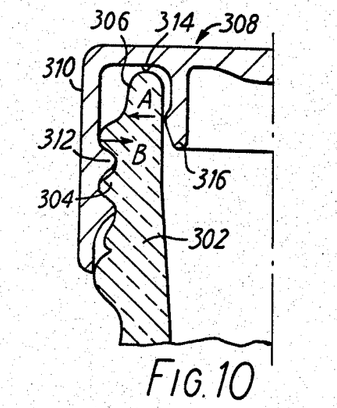
FIG. 10 is a radial cross-sectional view of a glass bottle neck with a plastics closure cap fitted thereon.

Referring now to FIG. 10, a glass bottle has a neck 302 provided with a finish in the form of a screwthread 304 and a terminal edge 306. A closure cap 308 of plastics material, typically polyethylene of a suitable grade, has an outer skirt 310 provided with a screw thread 312, and a top panel from which there depend the skirt 310, a sealing fin 314 and an inner spigot 316 which fits tightly within the bore of the bottle neck. The cap 308 is applied in a conventional capping machine to the bottle by a capping head of the machine which rotates the cap so as to screw it into position, the head applying a downward, axial compressive force to the cap and therefore to the bottle. As the spigot 316 is thus forced into the bottle neck, it becomes compressed and applies a radially-outward force A to the neck. When the cap is finally being tightened, a further force having a radially-inward component B is exerted on the outside of the neck by interaction of the screw threads 304 and 312. The axial distance between the radial planes in which the forces A and B appear represents the total length of the neck in which tensile hoop stresses resulting from the outward force A can be dissipated. This limitation can result in excessive strain, causing local cracking and/or shattering of the glass. In addition, there may also be ovality in the glass neck 312. The capping head is such as to restrain the outer skirt 310 in circular configuration, so that with respect to the oval-section neck there is a tendency for tensile forces to be exerted on the latter at its inside surface on the major axis and at its outside surface on the minor axis. These tensile forces may aggravate any tendency to fracture.

The foregoing is given as an example only of a type of cap with which fracture of the neck 302 within the cap may occur, but is not limiting. Fracture may occur or may be present for a variety of other reasons.

Figure 11:
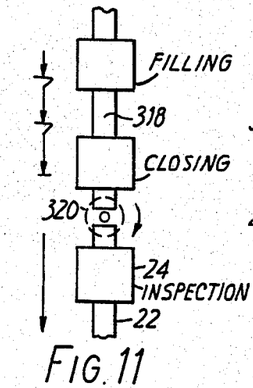
FIG. 11 is a diagram showing a sequence of operations in an industrial packaging operation.

A production line for filling the bottles with a product in a filling machine, and then applying the closure caps in a closing or capping machine, is indicated diagrammatically in FIG. 11. The bottles are carried to and from each machine by an indexing belt conveyor 318, which, after removing the bottles from the capping machine, delivers them via a suitable transfer device 320 (such as a star wheel) to a continuously-running conveyor 22, which carries the bottles through the monitoring or inspection unit 24 where the bottles are automatically inspected for cracks or other fractures, and the fractured bottles identified, in the same manner as has been described for empty bottles with reference to FIGS. 5 to 9.

Figure 12:
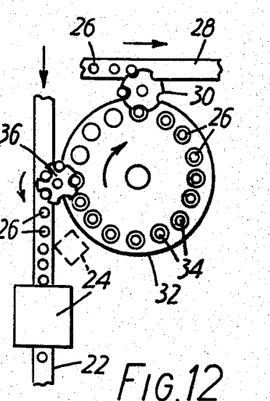
FIG. 12 is a diagram showing the sequence of operations in a similar operation using different equipment.

FIG. 12 shows another production line in which bottles 26, after being filled, are supplied by a feed conveyor 28 to a star wheel 30 which transfers the bottles to the continuously-rotating turret, indicated diagrammatically at 32, of a rotary closing machine having a number of closing heads 34 carried by the turret, whence the bottles are transferred by a second star wheel 36 to the conveyor 22 and thence to the inspecting unit 24 placed along the conveyor 22.

Figure 13:
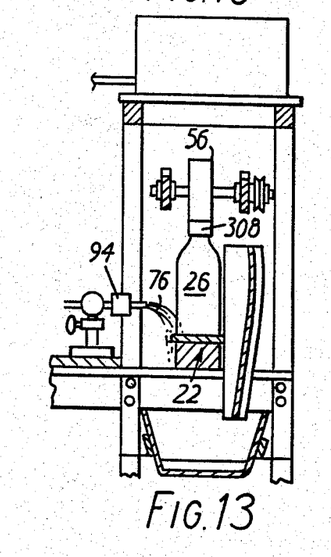
FIG. 13 is a view similar to FIG. 7, but showing a modified version of the inspection unit adapted for applying a simple axial force to filled and capped bottles, the caps on the bottles being generally of the kind illustrated in FIG. 10.

FIG. 13 shows a modification to FIG. 7, whereby a pure axial load is applied by a simple cylindrical roller 56 to the cap 308 of the bottle represented to FIG. 10. It should however be mentioned that whilst a pure axial applied force, without either rotation of the bottle or application of a force in a non-axial direction, is found to be sufficient in respect of bottles having caps generally as described with reference to FIG. 10, this is not the case with many other kinds of brittle articles to which the invention is applicable. Even with many kinds of capped container where it is required specifically to detect fractures within the neck, a radial load or torque may also be required.

Figure 14:
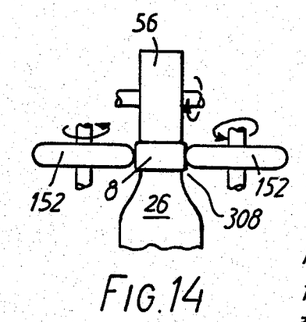
FIG. 14 is a diagrammatic representation of a modification to the apparatus of FIG. 13, in which a torque can be applied to the bottle caps.

FIG. 14 shows a pair of side rollers 152 rotatable in opposite directions to apply a torque to the bottle cap 308. The rollers 152 can if desired be biassed towards each other, for example by springs not shown, so as to apply radial forces as well as torque. If radial forces but no applied torque are required, the rollers 152 may be spring-biassed towards each other, but rotate in the same direction as each other instead of in opposite directions as indicated in FIG. 14.

Figure 15:
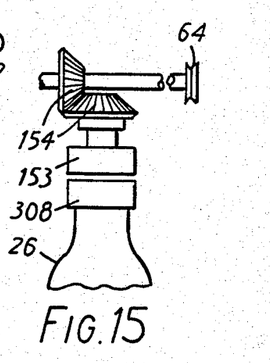
FIG. 15 is another diagrammatic representation, showing a modification to FIG. 14 whereby an applied axial load and applied torque are applied by a single force-applying member.

FIG. 15 illustrates a modification in which, in place of the axial force-applying roller 56 and radial torque rollers 152 of FIG. 14, a single head 153, rotated from the pulley 64, through gears 154, about its own vertical axis, applies both torque and axial force to the bottle 26 through the cap 8. The head 153 is carried by the frame 48 (shown in FIG. 7 but not in FIG. 15).

The conveyor 22 need not be in continuous motion, but may be of the indexing kind, whereby the article to be tested is stationary during the inspection process. In that case, an arrangement may be adopted such as is shown in FIG. 16, in which the article, 155, is raised at the inspection station by means of a lifter 156, into contact with a force-applying head 157, which again has an inclined article-engaging surface, but in which the latter has a frusto-conical form as indicated at 158, coaxial with the article 155.

Figures 16, 17, 18, 22:
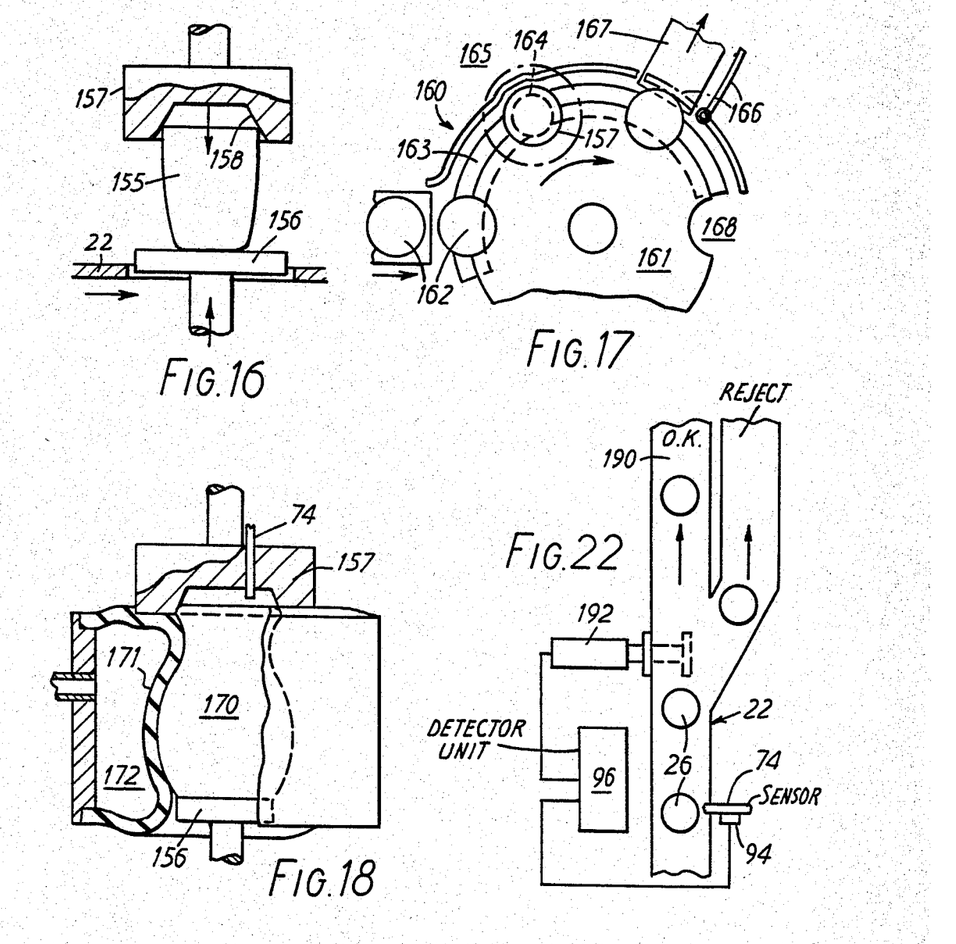
FIG. 16 is a diagram illustrating one embodiment of the automatic inspection of a brittle article when a series of such articles is advanced intermittently along an indexing conveyor.
FIG. 17 is a diagrammatic representation illustrating a similar principle to FIG. 16 but applied to an automatic inspection unit incorporating a rotating turret.
FIG. 18 illustrates one embodiment of an arrangement in which acoustic emission signals may be obtained during inspection of a hollow article to which axial and radial loads are applied over a major part of its outer surface.
FIG. 22 is a diagrammatic plan illustrating one form of rejection arrangement for articles rejected by an inspection unit according to the invention.

FIG. 17 shows the principle of intermittent conveying and stationary inspection applied to an inspection unit 160, in which, in place of the linear conveyor 22, there is provided an indexing turret 161 which carries the articles, 162, in an arc whilst they are supported on a fixed support guide 163. The latter is interrupted by a lifter 164 at the inspection station 165, below a head 157 similar to that shown in FIG. 16. The water pipe 74 of FIG. 5 and its associated equipment, are provided at the inspection station 165, but are not shown. In this example, in place of the marker 102 there is operated a gate 166 which operates to prevent the articles being ejected on to an acceptance conveyor 167 if a fault has been detected. Instead, faulty articles are carried on to a reject station 168, where they fall into a bin (not shown).

If a number of force-applying heads 157 are provided on the turret 161, with an associated, but optional lifter 164 also carried by the turret and suitably operated upon reaching the inspection station, it will be realised that the apparatus of FIG. 17 may be adapted for continuous (i.e. non-intermittent operation). In such a case, a fixed water stream manifold such as is shown at 250 in FIG. 23 will be provided.

In FIG. 18, the water pipe 74 extends through the head 157 in an arrangement modified from that shown in FIG. 16. The article, 170, being inspected in FIG. 18 is hollow, and of irregular curved external contours. The water stream is directed at the interior surface of the article 170, the whole of whose exterior surface is obscured by the head 157, lifter 156 and a radial force-applying member 171. The member 171 comprises a rubber membrane which is caused to apply radial force to, and to conform with the contours of, the article 170 by means of compressed air introduced momentarily into an annular chamber 172 whose inner, upper and lower walls are constituted by the membrane 171. The chamber 172 is deflated to allow release of the article 170.

Figure 20:
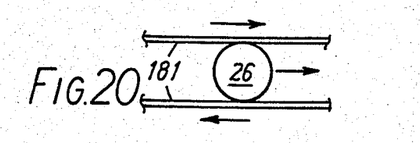
FIG. 20 is a simplified plan view on FIG. 19.
Figure 21:
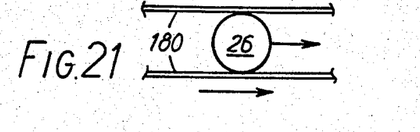
FIG. 21 is a simplified plan view taken on the line XXI—XXI in FIG. 19.

Yet another modification is shown in FIGS. 19 to 21, in which a bottle 26 is conveyed past the inspection station by a pair of parallel drive belts 180 and has a rotational torque imparted to it by a second pair of parallel belts 181, one of which moves in the opposite direction from the drive belt 180 on the same side of the bottle. Torsion may be applied to the bottle by addition of a pair of rollers 152, generally as already described with reference to FIG. 14. Both pairs of belts 180, 181 may be biassed towards each other so as to apply radial forces R to the bottle.

FIG. 22 shows a modification of the unit already described with reference to FIGS. 5 to 9. In FIG. 22 there are shown an acceptance branch 190 of the conveyor 22, and a rejection branch 191. Faulty articles 26 are diverted on to the rejection branch 191 of the conveyor by a pneumatic pusher 192, or a suitable deflector arm, operated by the detector unit 96 (as in FIG. 9) in place of the marker 102.

Figure 23:
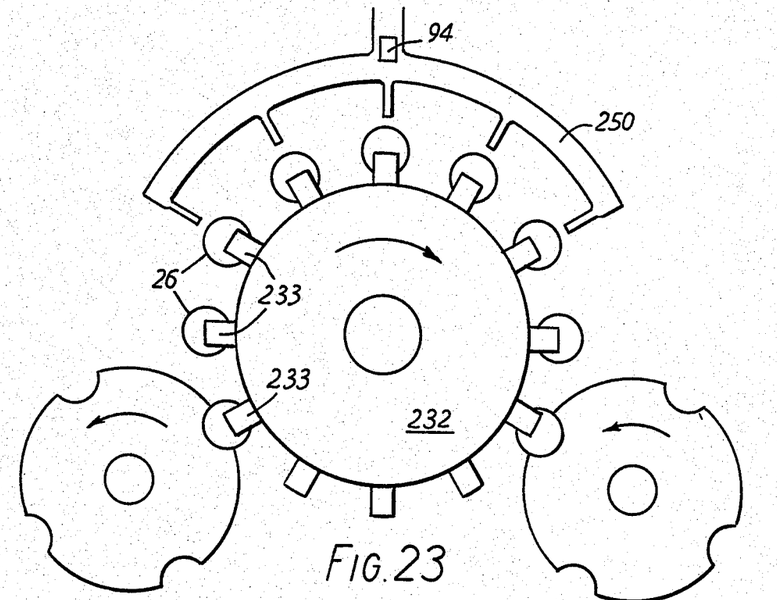
FIG. 23 is a diagrammatic plan view illustrating an application of one embodiment of the invention to a machine for applying closures to brittle containers.
Figure 26:
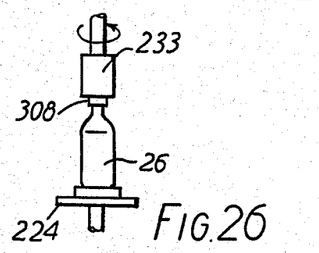
FIG. 26 is a diagrammatic elevation showing a closure cap being applied to a bottle.
Figure 27:
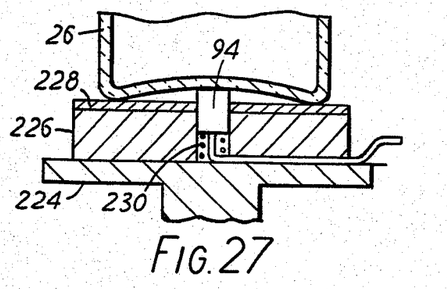
FIG. 27 is an enlarged sectional view illustrating one possible location for a sensor head of monitoring apparatus incorporated in a bottle capping machine, and representing also an alternative embodiment of means for detecting acoustic emission, as compared with that featured in a number of the other Figures.

The monitoring unit may be incorporated in a capping machine for brittle containers, so that the capping head itself provides the applied compressive load to the container; a second applied load, to propagate any fractures further, is then not required. Referring to FIGS. 23, 26 and 27, the turret 232 has a number of capping heads 233 for applying caps 308 to bottles 26. The machine includes a lifter 224 carrying a seat 226 having a rubber pad 228 on which the bottle 26 rests. FIG. 27 shows one possible position for the transducer or sensor head 94, viz. mounted in a central hole in the seat 226 and biassed upwardly by a spring 230 so as to be in close proximity to the base of the bottle. Suitable means are preferably provided for applying a liquid couplant, such as a suitable oil, to the top of the sensor unit 94 so as to provide a coupling between the latter and the bottle and so improve transmission of ultrasonic vibrations to the transducer. The output signals from the sensor unit, and from those from other sensor units in the turret, are then led to a multiplexing unit, not shown, which may be carried by the turret 232. The output from the multiplexing unit is transmitted to the main amplifier/processor (106, FIG. 9) by any suitable means (for example a slip ring on the turret main shaft), the crack detector unit 96 being preferably mounted away from the rotating turret. Means are provided on the capping machine for generating a timing pulse for each capping operation, so that a detected fracture can be associated with the appropriate container.

However, it is preferred to adapt the principle of water stream transmission of the ultrasonic vibrations to the capping machine incorporating the fault inspection method of the invention. To this end, in place of sensors mounted below the bottles as in FIG. 27, there is preferably provided a water manifold 250, FIG. 23, which directs a laminar stream of water at the bottle at each operative station of the capping machine, a single sensor 94 being mounted in the manifold 250, thus avoiding the need for multiplexing or for such expedients as slip rings.

Figure 24:
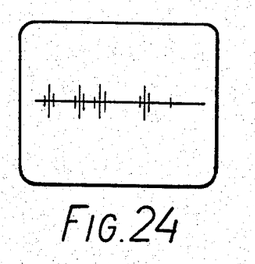
FIGS. 24 and 25 show static oscilloscope traces such as may be produced during capping operations using a machine of the kind shown in FIG. 23.
Figure 25:
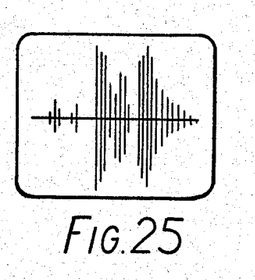

The visual display unit, if provided in apparatus according to the invention, may be arranged to operate intermittently, to show a separate, static, trace for each article being inspected. To this end a switching deivce (not shown in the drawings), to activate the visual display unit at the onset of the applied compressive load, may for example be controlled by a micro-switch, operated for example by the load arm 48 (FIG. 5). FIGS. 24 and 25 show typical static traces produced during a capping operation in apparatus as described with reference to FIG. 23: in FIG. 24 there is no fracture, so that the trace is of quite modest amplitude to indicate the stresses at various stages of the capping operation. In FIG. 25, on the other hand, traces of very large amplitude betray the occurrence of a crack during the capping operation.

Another possible modification in apparatus according to the invention is that, instead of using a water jet to transmit th acoustic emission from the container to the sensor head, the sensor head may be mounted on an arm in such a position that, at the inspecting station (e.g. at 46 in FIG. 5), the transducer wipes the container or its closure whilst the compressive load is being applied to the container. The arm is in this case resiliently mounted or is itself resilient.

In yet further embodiments the transducer may be mounted on the machine frame itself, for example in engagement with the shaft of the load wheel 50.

We claim:

1. A method of automatically inspecting an article of brittle material comprising the steps of:
    applying a load to the article;
    subjecting the article to a simple stream of liquid while the load is being applied, said stream being in free flow at a velocity such that the liquid is in laminar flow; and
    detecting any resulting acoustic emission from the article with a transducer in the stream so that said emission is transmitted to the transducer by the stream.

2. A method according to claim 1, characterised in that the stream of liquid (76) is continuous, the brittle article (26) being introduced into said stream.

3. A method according to claim 1, characterised in that the load (F) is applied compressively to the article (26) by effecting relative movement, axially a central axis of the article, as between the article and at least one force-applying member (50), the force-applying member or members being so shaped as to apply both axial and radial forces to the article.

4. A method according to claim 1, wherein the article (1) is of a shape defining a central axis (8) of the article, the method being characterised in that the step of applying a force to the article comprises applying a torque thereto about its central axis.

5. A method according to claim 4, characterised in that the article is rotated at least once about its central axis, at least whilst the force is being applied to the article whereby a radial component (R) of said force is directed over the entire periphery of the article.

6. A method according to claim 1, characterised in that said articles (26) are introduced in succession into said stream.

7. A method according to claim 1, wherein the stream is directed substantially horizontally.

8. Apparatus for automatically inspecting an article of brittle material, comprising
force-applying means for applying a load to the article,
a transducer for detecting any resulting acoustic emission from the article, and
flow means for directing a simple stream of liquid in laminar free flow against the article, the transducer being in or adjacent the flow means so that acoustic emission can be transmitted by said stream to the transducer, and the force-applying means being so arranged with respect to the flow means that said load is applied thereby to the article while the article is in contact with the stream.

9. Apparatus according to claim 8, characterised in that the force-applying means comprise a force-applying member (10) having at least one said force-applying surface (11) inclined with respect to a direction of relative linear movement between the force-applying member (10) and the article.

10. Apparatus according to claim 8, characterised in that the force-applying means (50) comprises a rolling member rotatable about its own axis and biassing means (52) operatively connected with the rolling member for applying a resilient biassing force thereto having a major component perpendicular to the axis of the rolling member.

11. Apparatus according to claim 8, having article-advancing means for moving a succession of generally-similar said articles carried thereby along a path, wherein the force-applying means comprises a rolling member (50) rotatable about its own axis and biassing means (52) operatively connected with the rolling member, the axis of the latter transverse with respect to the said path and the biassing means being arranged to apply a resilient biassing force to the rolling member having a major component perpendicular to said axis and to said path.

12. Apparatus according to claim 11, wherein the rolling member (50) has, for engaging each said article in turn, at least one coaxial force-applying surface (11) having a generator inclined with respect to said major component of the biassing force, whereby to apply said force to the article (26) in a direction such that the stresses induced in the latter have components both parallel and transverse to the said major component.

13. Apparatus according to claim 8, characterised in that the force-applying means comprises torque-applying means (150) for inducing a torque in the said article (26).

14. Apparatus according to claim 8 for inspecting a succession of generally similar articles, and further comprising conveyor means for conveying successive said articles past the flow means and into contact with the force-applying means, so that each article in turn is introduced into said stream and subjected to said load.

15. Apparatus according to claim 14 characterised in that the force-applying means comprises a pair of article-engaging members (150) movable in opposite directions for applying, to each said article (26) in turn, a torque about an axis perpendicular to the said path.

16. Apparatus according to claim 15, characterised in that the force-applying means comprises a pair of endless belts (150) each having an article-engaging portion generally parallel to said path, one of said portions being movable in the direction of advance of the articles along the path and the other said portion being movable in the opposite direction, whereby to apply to each article in turn a torque about an axis perpendicular to the said path.

* * * * *